United States Patent
Baraldi et al.

(10) Patent No.: US 7,750,049 B2
(45) Date of Patent: Jul. 6, 2010

(54) O-SUBSTITUTED-DIBENZYL UREA-DERIVATIVES AS TRPV1 RECEPTOR ANTAGONISTS

(75) Inventors: Pier Giovanni Baraldi, Ferrara (IT); Pier Andrea Borea, Ferrara (IT); Pierangelo Geppetti, Ferrara (IT); Francesca Fruttarolo, Ferrara (IT); Maria Giovanna Pavani, Ferrara (IT); Marcello Trevisani, Ferrara (IT)

(73) Assignee: Pharmeste S.R.L., Ferrara (IT)

( * ) Notice: Subject to any disclaimer, the term of this patent is extended or adjusted under 35 U.S.C. 154(b) by 0 days.

(21) Appl. No.: 12/519,753

(22) PCT Filed: Dec. 6, 2007

(86) PCT No.: PCT/IB2007/003784

§ 371 (c)(1),
(2), (4) Date: Jun. 17, 2009

(87) PCT Pub. No.: WO2008/075150

PCT Pub. Date: Jun. 26, 2008

(65) Prior Publication Data

US 2010/0105740 A1    Apr. 29, 2010

(30) Foreign Application Priority Data

Dec. 21, 2006   (EP)   .................. 06026533

(51) Int. Cl.
| | |
|---|---|
| A61K 31/535 | (2006.01) |
| A61K 31/497 | (2006.01) |
| A61K 31/44 | (2006.01) |
| A61K 31/335 | (2006.01) |
| A61K 31/195 | (2006.01) |
| A61K 31/17 | (2006.01) |

(52) U.S. Cl. ............. 514/595; 514/237.8; 514/252.12; 514/357; 514/452; 514/467; 514/564; 514/566; 544/168; 544/400; 546/332; 549/373; 549/452; 562/439; 564/56

(58) Field of Classification Search ............. 514/237.8, 514/252.12, 357, 452, 467, 564, 566, 595; 544/168, 400; 546/332; 549/373, 452; 562/439; 564/56

See application file for complete search history.

(56) References Cited

FOREIGN PATENT DOCUMENTS

| WO | 02/16318 | 2/2002 |
|---|---|---|
| WO | 2005/123666 | 12/2005 |

OTHER PUBLICATIONS

Rami Harshad K. "Discovery of SB-705498: A potent, selective and orally bioavailable TRPV1 antagonist suitable for clinical development," Bioorganic & Medicinal Chemistry Letter, Oxford, GB, vol. 16, No. 12, Jun. 15, 2006.
PCT International Search Report for PCT/IB2007/003784 filed on Jun. 12, 2007 in the name of Pharmeste S.R.L.
PCT Written Opinion for PCT/IB2007/003784 filed on Jun. 12, 2007 in the name of Pharmeste S.R.L.
PCT Notification of Transmittal of the International Preliminary Report on Patentability for PCT/IB2007/003784 filed on Jun. 12, 2007 in the name of Pharmeste S.R.L.

*Primary Examiner*—Peter G O'Sullivan
(74) *Attorney, Agent, or Firm*—Steinfl & Bruno

(57) ABSTRACT

The invention relates to compounds of formula (I) in which R is selected from halogen, alkyl, alkoxy, aryl and heteroaryl; $R_1$ is selected from 2-hydroxyethyl, 2,3-dihydroxypropyl, 3-hydroxypropyl, 2,2-dihydroxyethyl, 3,3-dihydroxypropyl, 1,3-dioxolane-ethyl, 1,3-dioxane-methyl, 1,3-dioxolane-methyl, 1,3-dioxane-ethyl, 3-fluoro-2-hydroxypropyl, 3-carboxy-2-hydroxy-propyl, 3-chloro-2-hydroxypropyl, 2-hydroxypropyl, 2-hydroxy-propen-2-yl, morpholinoethyl, piperazinoethyl, hydroxymethyl, benzyl, 4-(hydroxymethyl) benzyl, 4-chlorobenzyl, 4-fluorobenzyl, and 4-hydroxybenzyl. $R_2$ is tert-butyl or trifluoromethyl; R3 is independently selected from hydrogen, carboxy, cyano, alkyl or hydroxyalkyl, The compounds of formula (I) can be used for the preparation of pharmaceutical compositions for the therapy of inflammatory states, such as chronic neuropathic pain, over-active bladder syndrome, tumor pain, hemorrhoids, inflammatory hyperalgesia, post-intervention pain, dental extraction, airway and gastro-intestinal diseases.

(I)

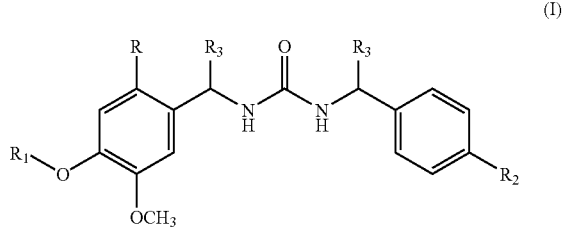

18 Claims, No Drawings

O-SUBSTITUTED-DIBENZYL UREA-DERIVATIVES AS TRPV1 RECEPTOR ANTAGONISTS

CROSS REFERENCE TO RELATED APPLICATIONS

The present application is the US national stage of International Application PCT/IB2007/003784 filed on Dec. 6, 2007 which, in turn, claims priority to European Application 06026533.7, filed on Dec. 21, 2006.

FIELD OF THE INVENTION

The present invention relates to vanilloid receptor antagonists, in particular to O-hydroxyalkyl dibenzyl urea-derivatives that antagonize the vanilloid TRPV1 receptor.

STATE OF THE ART

Recent experimental evidences have demonstrated that the expression of the vanilloid TRPV1 receptor (transient receptor potential channel) increases in the course of inflammatory states. This suggested that vanilloid receptor antagonists could be useful for the treatment of inflammatory pain states, for example chronic neuropathic pain, over-active bladder syndrome, hemorrhoids, inflammatory hyperalgesia, post-intervention pain, dental extraction, airway and gastro-intestinal diseases.

A number of vanilloid receptor antagonists are known; some of them derive from capsaicin and are referred to as capsaicinoid antagonists.

DESCRIPTION OF THE INVENTION

The present invention relates to compounds of formula (I) wherein:

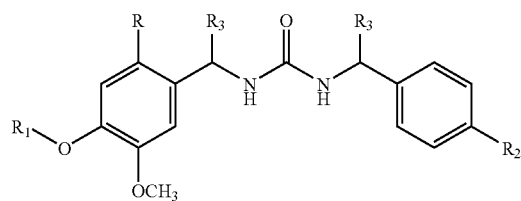

R is selected from halogen, alkyl, alkoxy, aryl and heteroaryl;

$R_1$ is selected from 2-hydroxyethyl, 2,3-dihydroxypropyl, 3-hydroxypropyl, 2,2-dihydroxyethyl, 3,3-dihydroxypropyl, 1,3-dioxolane-ethyl, 1,3-dioxane-methyl, 1,3-dioxolane-methyl, 1,3-dioxane-ethyl, 3-fluoro-2-hydroxypropyl, 3-carboxy-2-hydroxy-propyl, 3-chloro-2-hydroxypropyl, 2-hydroxy-propen-2-yl, morpholinoethyl, piperazinoethyl, hydroxymethyl, benzyl, 4-(hydroxymethyl)benzyl, 4-chlorobenzyl, 4-fluorobenzyl, and 4-hydroxybenzyl $R_2$ is tert-butyl or trifluoromethyl;

$R_3$ is independently selected from hydrogen, carboxy, cyano, alkyl or hydroxyalkyl, including all possible optical isomers and diastereisomers thereof.

For the purposes of the present application:
the term "halogen" indicates a halogen atom selected from fluorine, chlorine, bromine or iodine;
the term "alkyl" indicates a straight or branched ($C_1$-$C_4$) alkyl group;
the term "alkoxy" indicates a straight or branched ($C_1$-$C_4$) alkoxy group;
the term "aryl" indicated phenyl, optionally substituted with one or more halogen, alkyl, alkoxy groups as defined herein before, cyano or amino groups, which can be the same or different from one another;
the term "heteroaryl" indicates a 5- or 6-membered heterocycle containing one or more nitrogen, oxygen or sulphur atoms, which can be the same or different from one another, such as pyrrole, thiofene, furane, imidazole, thiazole, isothiazole, oxazole, pyridine or pyrimidine.

A first preferred group of compounds of formula (I) is that wherein:
R is chlorine or bromine;
$R_1$ is 2-hydroxyethyl;
$R_2$ is tert-butyl or trifluoromethyl;
$R_3$ is hydrogen.

A second group of preferred compounds of formula (I) is that wherein:
R is chlorine or bromine;
$R_1$ is 2,3-dihydroxypropyl;
$R_2$ is trifluoromethyl;
$R_3$ is hydrogen.

A third group of preferred compounds of formula (I) is that wherein:
R is methyl, phenyl, pyridine or 4-(substituted)-phenyl;
$R_1$ is (R)-(–)-2,3-dihydroxypropyl;
$R_2$ is trifluoromethyl;
$R_3$ is hydrogen.

A fourth group of preferred compounds of formula (I) is that wherein:
R is chlorine or bromine;
$R_1$ is (R)-(–)-2,3-dihydroxypropyl;
$R_2$ is trifluoromethyl;
$R_3$ is hydrogen.

Examples of particularly preferred compounds are
1-[4-(2-hydroxyethoxy)-2-bromo-5-methoxybenzyl]-3-[4-(trifluoromethyl)-benzyl]urea;
1-[4-(2-hydroxyethoxy)-2-chloro-5-methoxybenzyl]-3-[4-(trifluoromethyl)-benzyl]urea;
1-[4-(2-hydroxyethoxy)-2-bromo-5-methoxybenzyl]-3-[4-(tert-butyl)-benzyl]urea;
1-[4-(2-hydroxyethoxy)-2-chloro-5-methoxybenzyl]-3-[4-(tert-butyl)-benzyl]urea;
1-[4-(2,3-dihydroxypropoxy)-2-chloro-5-methoxybenzyl]-3-[4-(trifluoromethyl)-benzyl]urea;
1-[4-(2,3-dihydroxypropoxy)-2-bromo-5-methoxybenzyl]-3-[4-(trifluoromethyl)-benzyl]urea;
1-[4-((R)-(–)-2,3-dihydroxypropoxy)-2-chloro-5-methoxybenzyl]-3-[4-(trifluoromethyl)-benzyl]urea;
1-[4-((R)-(–)-2,3-dihydroxypropoxy)-2-phenyl-5-methoxybenzyl]-3-[4-(trifluoromethyl)-benzyl]urea;
1-[4-((R)-(–)-2,3-dihydroxypropoxy)-2-(pyridin-3-yl)-5-methoxybenzyl]-3-[4-(trifluoromethyl)-benzyl]urea;
1-[4-((R)-(–)-2,3-dihydroxypropoxy)-2-(4-chlorophenyl)-5-methoxybenzyl]-3-[4-(trifluoromethyl)-benzyl]urea;
1-[4-((R)-(–)-2,3-dihydroxypropoxy)-2-bromo-5-methoxybenzyl]-3-[4-(trifluoromethyl)-benzyl]urea.

The compounds of general formula (I) can be prepared by means of conventional methods, such as the reaction of a compound of formula (II), in which R, $R_1$ and $R_3$ are as defined above,

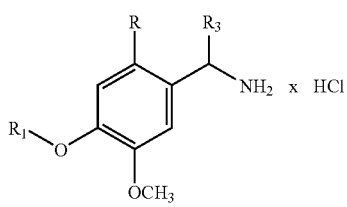

with a compound of formula (III) in which and $R_2$ and $R_3$ is as defined above:

The compounds of formula (I), their isomers and salts are able to inhibit the vanilloid TRPV1 receptor and can be used for the preparation of pharmaceutical compositions for the treatment of inflammatory states, chronic neuropathic pain, over-active bladder syndrome, hemorrhoids, inflammatory hyperalgesia, post-intervention pain, dental extraction, airway and gastro-intestinal diseases and tumour pain.

These formulations can be prepared by conventional methods and excipients, such as those disclosed in Remington's Pharmaceutical Sciences Handbook, XVII ed. Mack Pub., N.Y., USA.

The invention is hereinafter illustrated in greater detail in Scheme 1 and in the Examples.

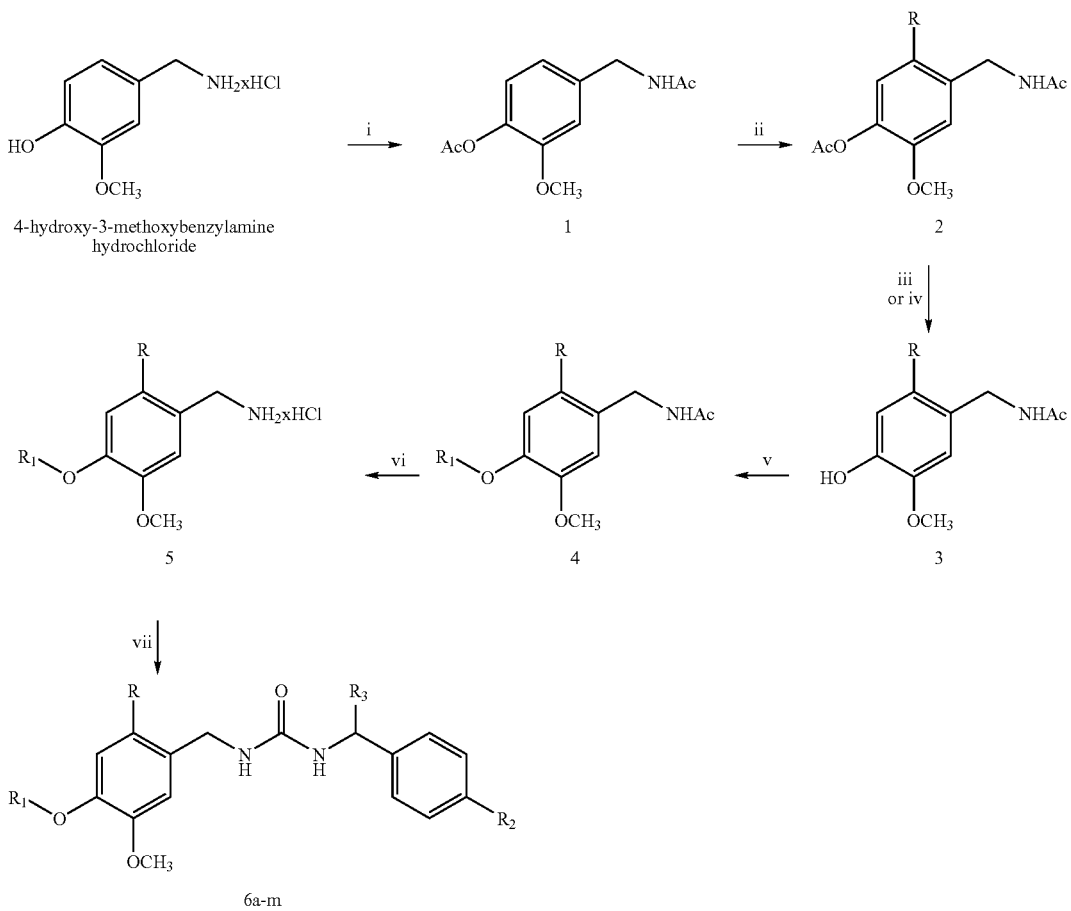

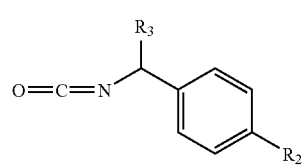

Reagents and conditions: (i) Acetic anidride, Pyr; (ii) NBS or NCS, DMF, 0° C.; (iii) aq. 10% HCl, Dioxane; (iv) when R=Br, Pd(PPh$_3$)$_4$, Na$_2$CO$_3$, boronic acid, DME, 90° C.; (v) hydroxyalkyl halide, K$_2$CO$_3$, DMF, 100° C.; (vi) HCl 37%, EtOH, Rfx; (vii) Triphosgene, 4-(substituted)benzyl amine, DIEA, CH$_2$Cl$_2$, 10 min.

Substituents: 6a: R=Cl, $R_1$=2-hydroxyethyl; $R_2$=tert-butyl, $R_3$=H; 6b: R=Br, $R_1$=2-hydroxyethyl; $R_2$=tert-butyl, $R_3$=H; 6c: R=Cl, $R_1$=2,3-dihydroxypropyl; $R_2$=trifluoromethyl, $R_3$=H; 6d: R=Br, $R_1$=2,3-dihydroxypropyl; $R_2$=trifluoromethyl, $R_3$=H; 6e: R=Cl, $R_1$=3-hydroxypropyl; $R_2$=trifluoromethyl, $R_3$=H; 6f: R=Cl, $R_1$=3-hydroxypropyl; $R_2$=tert-butyl, $R_3$=H; 6g: R=Cl, $R_1$=2-hydroxyethyl; $R_2$=trifluoromethyl, $R_3$=H; 6h: R=Br, $R_1$=2-hydroxyethyl; $R_2$=trifluoromethyl, $R_3$=H; R=Phenyl, $R_1$=2,3-dihydroxypropyl; $R_2$=trifluoromethyl; $R_3$=H; 6l: R=Pyridin-3-yl, $R_1$=2,3-dihydroxypropyl; $R_2$=trifluoromethyl; $R_3$=H; 6m: R=4-(chloro)-phenyl, $R_1$=2,3-dihydroxypropyl; $R_2$=trifluoromethyl; $R_3$=H.

EXAMPLES

The reactions were routinely monitored by thin-layer chromatography (TLC) on silica gel (precoated $F_{245}$ Merck plates) and the products were visualized with an iodine or potassium permanganate solution. $^1$H NMR spectra were recorded in $CDCl_3$, $CF_3COOD$ or DMSO-$d_6$ with a Varian VXR 200 spectrometer. Peak positions are given in parts per million (δ) downfield from tetramethylsilane as internal standard, and J values are given in Hz. IR spectra were recorded on a Pye Unicam SP 300 spectrometer using the KBr Wafer technique. Mass spectra were obtained with a Shimadzu QP5050 DI 50 spectrometer. The expression "Light petroleum ether" refers to the petroleum fraction boiling at 40-60° C. Melting points (M.p.) were determined on a Buchi-Tottoli instrument and are uncorrected. Chromatographies were performed using Merck 60-200 mesh silica gel. The synthesized compounds showed $^1$H NMR spectra in agreement with the assigned structures. Elemental analyses were within ±0.4% of the theoretical values for C, H and N.

Example 1

1.1. Synthesis of 4-acetoxy-3-methoxy-N-acetyl-benzylamine

Acetic anhydride (1 ml, 10.5 mmol) was added to a solution of 4-hydroxy-3-methoxy-benzylamine hydrochloride (0.5 g, 2.63 mmol) in pyridine (5 ml) and the mixture was stirred at room temperature for 6 hours. The solvent was evaporated off under reduced pressure and the residue was suspended in water (100 ml). The aqueous layer was extracted with ethyl acetate (3×20 ml) and the combined organic phases were anhydrified ($Na_2SO_4$) and evaporated under reduced pressure to afford the title compound as white solid (0.45 g, yield 75%).

$^1$H-NMR ($CDCl_3$) δ 2.01 (s, 3H, $CH_3$), 2.31 (s, 3H, $CH_3$), 3.81 (s, 3H, $OCH_3$), 4.38 (d, 2H, J=6, $CH_2$), 5.90 (bs, 1H, NH), 6.90 (m, 3H, aromatic).

MS: m/z 238.1 ($M^+$ $C_{12}H_{15}NO_4$).

1.2. Synthesis of 2-bromo-4-acetoxy-5-methoxy-N-acetyl benzylamine

N-bromosuccinimide (6.3 mmol, 1.1 g) was added to a solution of 4-acetoxy-3-methoxy-N-acetyl-benzylamine of Example 1.1 (1.5 g, 4.2 mmol) in dry DMF (8 ml) and the mixture was stirred for 30' at 0° C. and then for 16 hours at room temperature.

The formation of a white precipitate was observed when water (40 ml) was added to the reaction.

The solid was filtered off and washed twice with cold water (2×20 ml), then dried over $P_2O_5$ to afford the title compound as white solid (1.4 g, 99% yield).

$^1$H NMR (DMSO-$d_6$) δ 1.89 (s, 3H), 2.24 (s, 3H), 3.76 (s, 3H, $OCH_3$), 4.27 (d, 2H, $CH_2$, J=8), 7.09 (s, 1H, aromatic), 7.25 (s, 1H, aromatic), 8.35 (t, 1H, NH).

Bidimensional NOESY (DMSO-$d_6$): coupling between the singlet at 2.24 ppm and the singlet at 7.25 ppm confirms that bromine is at the 2-position of the aromatic ring.

MS: m/z 316 ($M^+$ $C_{12}H_{14}BrNO_4$).

Example 2

2. General Procedure for the synthesis of 2-(phenyl/pyridine-3-yl/4-(chloro)phenyl)-4-hydroxy-5-methoxy-N-acetyl benzylamine A solution of 2-bromo-4-acetoxy-5-methoxy-N-acetyl benzylamine (600 mg, 1.9 mmol) in DME (15 mL) was deoxygenated by passing $N_2$ through the mixture for 5 min. Then was added $Pd(PPh_3)_4$ (0.09 mol eq) and a solution of the appropriate boronic acid (1.4 mol eq) in abs. ethanol (3 mL). The mixture was stirred for 10 min. then a 2M aq. solution of $Na_2CO_3$ (9 mL) was added and the reaction was heated at 90° C. for 12 h. The solvent was evaporated at reduced pressure, water was added (60 mL) and the aqueous phase was extracted with EtOAc (3×30 mL). The recombined organic phased were anhydrified over $Na_2SO_4$, evaporated and the residue was purified by chromatography (6:4 EtOAc:petroleum ether) to afford the title compounds as solids.

2.1. 2-phenyl-4-hydroxy-5-methoxy-N-acetyl benzylamine

White solid, yield 95%.
$^1$H NMR ($CDCl_3$) δ 1.89 (s, 3H), 3.92 (s, 3H), 4.33 (d, 2H, J=4.4), 5.41 (bs, 1H), 5.75 (s, 1H), 6.84 (s, 1H), 6.94 (s, 1H), 7.41-7.29 (m, 5H).
MS: m/z 271 ($M^+$ $C_{16}H_{17}NO_3$).

2.2. 2-(pyridine-3-yl)-4-hydroxy-5-methoxy-N-acetyl benzylamine

Pale yellow solid, yield 68%.
$^1$H NMR (DMSO-$d_6$) δ 1.79 (s, 3H), 3.79 (s, 3H), 4.04 (d, 2H, J=4), 6.65 (s, 1H), 6.98 (s, 1H), 7.42 (m, 1H), 7.71 (m, 1H), 8.41 (bt, 1H), 8.54 (m, 1H), 9.19 (s, 1H).
MS: m/z 272 ($M^+$ $C_{15}H_{16}N_2O_3$).

2.2. 2-(4-chloro)phenyl-4-hydroxy-5-methoxy-N-acetyl benzylamine

Pale yellow solid, yield 78%.
$^1$H NMR (DMSO-$d_6$) δ 1.81 (s, 3H), 3.79 (s, 3H), 4.08 (d, 2H, J=4), 6.01 (t, 1H), 6.79 (s, 1H), 6.98 (s, 1H), 7.44 (dd, 4H), 8.15 (s, 1H).
MS: m/z 305 ($M^+$ $C_{16}H_{16}ClNO_3$).

Example 3

3.1. Synthesis of 2-bromo-4-hydroxy-5-methoxy-N-acetyl benzylamine

10% Aq. hydrochloric acid (2.5 ml) was added to a solution of 2-bromo-4-acetoxy-5-methoxy-N-acetyl-benzylamine 2 (0.45 g, 1.66 mmol) in dioxane (15 ml) and the mixture was refluxed for 2 hours, then cooled and the solvent was concentrated under vacuum and the residue was basified with 10% aq. NaOH. The resulting solid was collected by filtration, washed with cold water and dried to furnish the title compound as white solid in quantitative yield.

¹H NMR (DMSO-d$_6$) δ 2.18 (s, 3H, CH$_3$), 3.87 (s, 3H, OCH$_3$), 4.00 (d, 2H, CH$_2$), 6.91 (s, 1H, aromatic), 7.32 (s, 1H, aromatic), 8.46 (t, 3H, NH$_2$), 9.80 (bs, 1H, OH).

M.p.: >300° C.

3.2. Synthesis of 2-bromo-4-(2-hydroxyethoxy)-5-methoxy-N-acetyl benzylamine To a solution of compound 3 (0.4 g, 1.46 mmol) in dry DMF (15 ml) dry K$_2$CO$_3$ (2 mol eq) and 2-iodoethanol (2 mol eq) were added. The mixture was refluxed for 6 hours, then the solvent was evaporated off under reduced pressure. After addition of water the aqueous layer was extracted with EtOAc (3×25 ml) and the organic phases were anhydrified over Na$_2$SO$_4$ and evaporated under reduced pressure to furnish the title compound as pale yellow solid (0.38 g, 81% yield).

¹H NMR (CDCl$_3$) δ 2.00 (s, 3H), 3.84 (s, 3H), 3.92 (t, 2H, J=2), 4.09 (t, 2H, J=2.1), 4.44 (d, 2H, J=4), 5.21 (t, 1H), 5.90 (bs, 1H), 6.96 (s, 1H), 7.07 (s, 1H).

3.3. Synthesis of 2-bromo-4-(2-hydroxyethoxy)-5-methoxy-benzylamine hydrochloride 37% Hydrochloric acid (0.2 ml) was added to a solution of 2-bromo-4-(2-hydroxyethoxy)-5-methoxy-N-acetyl benzylamine 4 (0.1 g, 0.31 mmol) in abs. ethanol (5 ml) and the mixture was refluxed for 12 hours. After cooling, the solvent was evaporated off under reduced pressure and the residue was recrystallized from a methanol/ethyl ether mixture to afford the title compound as pale yellow solid in quantitative yield.

¹H NMR (DMSO-d$_6$) δ 3.95 (s, 3H), 4.14 (t, 2H, J=2), 4.19 (m, 2H,), 5.01 (m, 2H,), 5.44 (t, 1H), 7.02 (s, 1H), 7.27 (s, 1H), 7.38 (m, 3H).

Example 4

General Procedure for the synthesis of 2-(phenyl/pyridine-3-yl/4-(chloro)phenyl)-4-(2,3-d hydroxypropoxy)-5-methoxy-N-acetyl benzylamine To a solution of 2-(phenyl/pyridine-3-yl/4-(chloro)phenyl)-4-hydroxy-5-methoxy-N-acetyl benzylamine (1.1 mmol) in dry DMF (10 ml) dry K$_2$CO$_3$ (2 mol eq) and 3-chloro-1,2-dihydroxypropane (2 mol eq) were added. The mixture was refluxed for 12 hours, then the solvent was evaporated off under reduced pressure. After addition of water the aqueous layer was extracted with EtOAc (3×25 ml) and the organic phases were washed with NaOH 3% (20 mL), anhydrified over Na$_2$SO$_4$ and evaporated under reduced pressure to furnish the title compound as solids after crystallization from Et$_2$O.

4.1. 2-phenyl-4-(2,3-dihydroxypropoxy)-5-methoxy-N-acetyl benzylamine

Pale yellow solid, yield 72%.

¹H NMR (DMSO-d$_6$) δ 1.83 (s, 1H), 3.44 (t, 2H), 3.79 (s, 1H), 3.95 (m, 7H), 4.10 (d, 2H, J=4.2), 4.62 (t, 1H), 4.92 (d, 1H), 6.79 (s, 1H), 6.98 (s, 1H), 7.36 (m, 5H), 8.16 (t, 1H).

4.2. 2-(pyridine-3-yl)-4-(2,3-dihydroxypropoxy)-5-methoxy-N-acetyl benzylamine Pale yellow solid, yield 60%.

¹H NMR (DMSO-d$_6$) δ 1.80 (s, 3H), 3.44 (t, 2H), 3.80 (s, 3H), 3.96 (m, 3H), 4.08 (d, 2H), 4.62 (t, 1H), 4.93 (d, 1H), 6.84 (s, 1H), 7.02 (s, 1H), 7.44 (m, 1H), 7.77 (m, 1H), 8.20 (bt, 1H), 8.56 (m, 2H).

4.3. 2-(4-chloro)-phenyl-4-(2,3-dihydroxypropoxy)-5-methoxy-N-acetyl benzylamine Pale yellow solid, yield 65%.

¹H NMR (DMSO-d$_6$) δ 1.81 (s, 3H), 3.42 (d, 3H), 3.79 (s, 3H), 3.90 (m, 4H), 4.08 (d, 2H), 6.79 (s, 1H), 6.98 (s, 1H), 7.45 (dd, 4H), 8.20 (bt, 1H).

Example 5

5.1. Synthesis of 2-bromo-4-(2,3-dihydroxypropoxy)-5-methoxy-N-acetyl benzylamine To a solution of 2-bromo-4-hydroxy-5-methoxy-N-acetyl benzylamine 3 (0.3 g, 1.1 mmol) in dry DMF (10 ml) dry K$_2$CO$_3$ (2 mol eq) and 3-chloro-1,2-dihydroxypropane (2 mol eq) were added. The mixture was refluxed for 6 hours, then the solvent was evaporated off under reduced pressure. After addition of water the aqueous layer was extracted with EtOAc (3×25 ml) and the organic phases were anhydrified over Na$_2$SO$_4$ and evaporated off under reduced pressure to furnish the title compound as pale yellow solid (0.35 g, 84% yield).

¹H NMR (DMSO-d$_6$) δ 1.88 (s, 3H), 3.44 (t, 2H), 3.74 (s, 3H), 3.88-3.96 (m, 3H), 4.22 (d, 2H, J=6), 4.66 (t, 1H), 4.96 (d, 1H, J=6), 6.93 (s, 1H), 7.14 (s, 1H), 8.25 (t, 1H).

5.2. Synthesis of 2-bromo-4-(2,3-dihydroxypropoxy)-5-methoxy-benzylamine hydrochloride 37% Hydrochloric acid (0.3 ml) was added to a solution of 2-bromo-4-(2,3-dihydroxypropoxy)-5-methoxy-N-acetyl benzylamine 4 (0.3 g, 0.86 mmol) in abs. ethanol (12 ml) and the mixture was refluxed for 12 hours. After cooling, the solvent was evaporated off under reduced pressure and the residue was recrystallized from a methanol/ethyl ether mixture to afford the title compound as pale orange solid in quantitative yield.

¹H NMR (DMSO-d$_6$) δ 3.42 (t, 2H), 3.74 (s, 3H), 3.74-3.95 (m, 4H), 4.21 (d, 2H, J=6), 4.98 (m, 4H), 7.13 (s, 1H), 7.38 (s, 1H).

Example 6

General Procedure for the synthesis of 2-(phenyl/pyridine-3-yl/4-(chloro)phenyl)-4-(2,3-dihydroxypropoxy)-5-methoxy-benzylamine hydrochloride 37% Hydrochloric acid (5 ml) was added to a solution of 2-(phenyl/pyridine-3-yl/4-(chloro)phenyl)-4-(2,3-dihydroxypropoxy)-5-methoxy-N-acetyl benzylamine (8 mmol) in abs. ethanol (25 ml) and the mixture was refluxed for 12 hours. After cooling, the solvent was evaporated off under reduced pressure and the residue was recrystallized from a methanol/ethyl ether mixture to afford the title compound solids in a quantitative yield.

6.1. Synthesis of 2-chloro-4-acetoxy-5-methoxy-N-acetyl benzylamine

N-chlorosuccinimide (3.15 mmol, 0.42 g) was added to a solution of 4-acetoxy-3-methoxy-N-acetyl-benzylamine of Example 1.1 (0.5 g, 2.1 mmol) in dry DMF (6 ml) and the mixture was stirred for 30' at 0° C. and then for 16 hours at room temperature.

When water was added to the reaction (40 ml) the formation of a white precipitate was observed.

The solid was filtered off and washed twice with cold water (2×20 ml), then dried over $P_2O_5$ to afford the title compound as white solid (0.45 g, 83% yield).

$^1$H NMR (DMSO-$d_6$) δ 1.85 (s, 3H), 2.21 (s, 3H), 3.74 (s, 3H, OCH$_3$), 4.21 (d, 2H, CH$_2$, J=8), 7.01 (s, 1H, aromatic), 7.22 (s, 1H, aromatic), 8.32 (t, 1H, NH).

Bidimensional NOESY (DMSO-$d_6$): coupling between the singlet at 2.21 ppm and the singlet at 7.22 ppm confirms that chlorine is at the 2-position of the aromatic ring.

MS: m/z 272.1 ($M^+$ $C_{12}H_{14}ClNO_4$).

6.2. Synthesis of 2-chloro-4-hydroxy-5-methoxy-N-acetyl benzylamine

10% Aq. hydrochloric acid (2.5 ml) was added to a solution of 2-chloro-4-acetoxy-5-methoxy-N-acetyl-benzylamine 2 (0.45 g, 1.66 mmol) in dioxane (15 ml) and the mixture was refluxed for 2 hours. After cooling, the solvent was reduced under vacuum and the residue was basified with 10% aq. NaOH. The resulting solid was collected by filtration, washed with cold water and dried to furnish the title compound as white solid in quantitative yield.

$^1$H NMR (DMSO-$d_6$) δ 2.15 (s, 3H, CH$_3$), 3.82 (s, 3H, OCH$_3$), 3.99 (d, 2H, CH$_2$), 6.86 (s, 1H, aromatic), 7.30 (s, 1H, aromatic), 8.41 (t, 3H, NH$_2$), 9.77 (bs, 1H, OH).

M.p.: >300° C.

6.3. Synthesis of 2-chloro-4-(2,3-dihydroxypropoxy)-5-methoxy-N-acetyl benzylamine Dry $K_2CO_3$ (2 mol eq) and 2-iodoethanol (2 mol eq) were added to a solution of 2-chloro-4-hydroxy-5-methoxy-N-acetyl benzylamine 3 (0.4 g, 1.46 mmol) in dry DMF (15 ml). The mixture was refluxed for 6 hours, then the solvent was evaporated off under reduced pressure. After addition of water the aqueous layer was extracted with EtOAc (3×25 ml) and the organic phases were anhydrified over $Na_2SO_4$ and evaporated under reduced pressure to furnish the title compound as pale yellow solid (0.38 g, 81% yield).

$^1$H NMR (CDCl$_3$) δ 2.00 (s, 3H), 3.84 (s, 3H), 3.92 (t, 2H, J=2), 4.09 (t, 2H, J=2.1), 4.44 (d, 2H, J=4), 5.21 (t, 1H), 5.90 (bs, 1H), 6.96 (s, 1H), 7.07 (s, 1H).

6.4. Synthesis of 2-chloro-4-(2,3-dihydroxypropoxy)-5-methoxy-benzylamine hydrochloride 37% Hydrochloric acid (0.2 ml) was added to a solution of 2-bromo-4-(2-hydroxyethoxy)-5-methoxy-N-acetyl benzylamine 4 (0.1 g, 0.31 mmol) in abs. ethanol (5 ml) and the mixture was refluxed for 12 hours. After cooling, the solvent was evaporated off under reduced pressure and the residue was recrystallized from a mixture of methanol/ethyl ether to afford the title compound as pale yellow solid in quantitative yield.

Example 7

General procedure for the synthesis of compounds 6a-6m

Triphosgene (0.37 mol eq) was dissolved in $CH_2Cl_2$ (3 ml). A mixture of 4-tert-butyl/trifluoromethyl benzyl amine (0.33 mmol) and DIEA (2.2 mol eq) in $CH_2Cl_2$ (2 ml) was slowly added to the stirred solution of triphosgene over a period of 30 min. using a syringe pump. After 5 min a solution of a suitable amine hydrochloride 5 (0.33 mmol) was added in one portion. The reaction mixture was stirred at room temperature for 2-4 h, evaporated under reduced pressure, diluted with EtOAc (20 ml), washed with 10% aq. KHSO$_4$, 5% aq. NaHCO$_3$ and brine, dried over Na$_2$SO$_4$ and evaporated to dryness. The residue was purified by flash chromatography (100% EtOAc) to furnish the title compound as solid.

7.1. 1-[4-(2-Hydroxyethoxy)-2-bromo-5-methoxy-benzyl]-3-[4-(tert-butyl)-benzyl]urea 6b $^1$H NMR (DMSO-$d_6$) δ 1.26 (s, 9H), 3.37 (s, 3H), 3.70 (m, 4H), 3.98 (t, 2H, J=2), 4.61 (bs, 4H), 4.87 (t, 1H, J=2.1), 6.98 (bs, 1H), 7.21 (s, 1H), 7.23 (d, 2H, J=7.8), 7.34 (d, 2H, J=8), 7.80 (bs, 1H), 8.00 (bs, 1H).

Mp: 138° C.

MS: m/z 481.4 ($M^+$ $C_{22}H_{29}BrN_2O_3S$).

7.2. 1-[4-(2,3-Dihydroxypropoxy)-2-chloro-5-methoxybenzyl]-3-[4-(trifluoromethyl)-benzyl]urea 6c White solid, yield 80%.

$^1$H NMR (DMSO-$d_6$) δ 3.44 (t, 2H, J=6), 3.68 (s, 1H), 3.74-4.00 (m, 5H), 4.22 (d, 2H, J=6), 4.32 (d, 2H, J=6), 4.67 (t, 1H), 4.94 (d, 1H), 6.45 (bt, 1H), 6.65 (bt, 1H), 6.90 (s, 1H), 7.00 (s, 1H), 7.48 (d, 2H, J=7.8), 7.69 (d, 2H, J=8).

MS: m/z 462 ($M^+$ $C_{20}H_{22}ClF_3N_2O_5$).

Mp: 154-5° C.

(R)-(−)6c: $[\alpha]_D^{20}$=−8.33 (95% EtOH).

7.3. 1-[4-(2,3-Dihydroxypropoxy)-2-bromo-5-methoxybenzyl]-3-[4-(trifluoromethyl)-benzyl]urea 6d White solid, yield 84%.

$^1$H NMR (DMSO-$d_6$) δ 3.41 (t, 2H, J=6), 3.74 (s, 1H), 4.00-3.85 (m, 5H), 4.19 (d, 2H, J=6), 4.32 (d, 2H, J=6), 4.62 (t, 1H), 4.95 (d, 1H), 6.49 (bt, 1H), 6.68 (bt, 1H), 6.90 (s, 1H), 7.13 (s, 1H), 7.45 (d, 2H, J=7.8), 7.65 (d, 2H, J=8).

MS: m/z 507 ($M^+$ $C_{20}H_{22}BrF_3N_2O_5$).

Mp: 164° C.

(R)-(−)6d: $[\alpha]_D^{20}$=−8.5 (95% EtOH).

7.4. 1-[4-(2-Hydroxyethoxy)-2-bromo-5-methoxy-benzyl]-3-[4-(trifluoromethyl)-benzyl]urea 6h White solid, yield 73%.

$^1$H NMR (DMSO-$d_6$) δ 3.67 (s, 3H), 3.47 (m, 2H), 3.94 (t, 2H, J=4), 4.16 (d, 2H, J=6), 4.32 (d, 2H, J=6), 4.85 (t, 1H, J=2), 6.52 (bt, 1H), 6.68 (bt, 1H), 6.90 (s, 1H), 7.14 (s, 1H), 7.49 (d, 2H, J=8), 7.65 (d, 2H, J=8).

MS: m/z 477 ($M^+$ $C_{19}H_{20}BrF_3N_2O_4$).

Mp: 162° C.

7.5. 1-[4-(2,3-dihydroxypropoxy)-2-phenyl-5-methoxybenzyl]-3-[4-(trifluoromethyl)-benzyl]urea 6i White solid, yield 35%.
$^1$H NMR (DMSO-d$_6$) δ 3.41 (t, 2H), 3.78 (s, 3H), 4.06 (m, 3H), 4.23 (d, 2H), 4.26 (d, 2H), 4.61 (t, 1H), 4.95 (d, 1H), 6.40 (t, 1H), 6.51 (t, 1H), 6.80 (s, 1H), 6.99 (s, 1H), 7.36 (m, 7H), 7.68 (d, 2H).
MS: m/z 504 (M$^+$ C$_{26}$H$_{27}$F$_3$N$_2$O$_5$).
Mp: 168° C.

7.6. 1-[4-(2,3-dihydroxypropoxy)-2-(pyridin-3-yl)-5-methoxybenzyl]-3-[4-(trifluoromethyl)-benzyl]urea 6l Pale yellow solid, yield 30%.
$^1$H NMR (DMSO-d$_6$) δ 3.44 (t, 2H), 3.75 (s, 3H), 3.91 (m, 4H), 4.05 (d, 2H, J=4.3), 4.29 (d, 2H, J04.2), 4.61 (t, 1H), 4.92 (d, 1H), 6.51 (m, 2H), 6.84 (s, 1H), 7.03 (s, 1H), 4.45 (m, 3H), 7.68 (d, 2H), 7.77 (m, 1H), 8.56 (m, 1H).
MS: m/z 505 (M$^+$ C$_{25}$H$_{26}$F$_3$N$_3$O$_5$).
Mp: 201° C.

7.7. 1-[4-(2,3-dihydroxypropoxy)-2-(4-chloro)phenyl-5-methoxybenzyl]-3-[4-(trifluoromethyl)-benzyl]urea 6m White solid, yield 45%.
$^1$H NMR (DMSO-d$_6$) δ 3.44 (t, 2H), 3.74 (s, 3H), 3.93 (m, 4H), 4.07 (d, 2H), 4.30 (d, 2H), 4.62 (t, 1H), 4.92 (d, 1H), 6.41 (m, 2H), 6.78 (s, 1H), 6.98 (s, 1H), 7.43 (m, 6H), 7.69 (d, 2H).
MS: m/z 538 (M$^+$ C$_{26}$H$_{26}$ClF$_3$N$_2$O$_5$).
Mp: 174° C.

Biological Assays

Animals

In vivo experiments were conducted with PharmEste srl (Ferrara, Italy) and with the University of Ferrara, following protocols approved by the Animal Care and Use Committee of the University of Ferrara.

Radioligand Binding Assay

Male Sprague-Dawley rats with body weight between 250 to 350 g were used. For binding assays the rats were decapitated under anesthesia and the spinal cord was removed and disrupted using a Polytron tissue homogenizer in ice cold buffer containing 5 mM KCl, 5.8 mM NaCl, 0.75 mM CaCl$_2$, 2 mM MgCl$_2$, 320 mM sucrose, 10 mM Hepes, pH 8.6 (Szallasi and Blunberg, 1992; 1993). In competition experiments, the membranes were incubated at 37° C. for 60 min with [$^3$H]RTX (0.4 nM) and with increasing concentrations of test compounds in the range from 0.1 nM to 3 μM. Non-specific binding was evaluated in the presence of 1 μM RTX. Saturation and competition studies were analyzed with the Ligand program (Bradford, 1976; Munson and Rodbard, 1980).

Ca$^{2+}$ Fluorescence Measurements in Cultured Rat Trigeminal Ganglia

The calibration curve was determined using a buffer containing Fura-2-AM-ester and definite concentrations of free Ca$^{2+}$. This curve was then used to convert the data obtained from F$_{340}$/F$_{380}$ ratio to [Ca$^{2+}$]$_i$ (nM) (Kudo, Y). The effects of pretreatments with compounds 6a-6m on the increase in [Ca$^2$]$_i$ produced by 30 nM capsaicin were studied.

Capsaicin-Induced Secondary Allodynia in Rat

Capsaicin (5 nmols/50 μl/paw) was injected in the plantar surface of the glabrous skin of the right paw of rats anesthetized with diethyl ether (Chaplan et al., 1994). Compounds 6c and 6d were orally administrated 2 hours prior to capsaicin injection. Tactile allodynia was evaluated 90 min after capsaicin challenge.

Reagents

The stock concentrations of capsaicin (10 mM) was prepared in absolute ethanol. Compounds 6a-6m were prepared in 50% DMSO and 50% Tween 80. Fura-2-AM-ester and ionomycin were dissolved in 100% DMSO. All the other drugs were dissolved in distilled water. The appropriate dilutions were then made in Krebs buffer solution.

Results

Radioligand Binding Assays

Compounds 6a-6m displaced [$^3$H]RTX from its binding site in rat spinal cord membranes at low concentrations, as indicated by the K$_i$ values reported in Table 1.

Ca$^{2+}$ Fluorescence Assay

Capsaicin (30 nM) increased [Ca$^{2+}$]$_i$ in the vast majority (95%) of rat trigeminal neuron cells, which were therefore identified as TRPV1-expressing neurons. IC$_{50}$ values of inhibiting capsaicin-evoked [Ca$^{2+}$]$_i$ mobilization are summarized in Table 1.

TABLE 1

K$_i$ and IC$_{50}$ values of some representative compounds of the invention.

| | Code | | | | | | | | | |
|---|---|---|---|---|---|---|---|---|---|---|
| | 6a | 6b | 6c | 6d | 6e | 6f | 6g | 6h | 6i | 6l | 6m |
| K$_i$ (nM) | 175 | 76 | 60 | 86 | >1000 | 253 | >1000 | 150 | 273 | 172 | 117 |
| IC$_{50}$ (nM) | 859 | 61 | 10.2 | 80 | >1000 | 500 | 164 | 119 | >1000 | >1000 | nt |

The (R)-(−) and (S)-(+)-isomers of compounds 6c and 6d were also synthesized in order to appreciate the difference in activity with the respect to the racemic compounds. The most active isomer was the (R)-(−) form whereas as the (S)-(+)-form was at least 300 fold less active as shown in Table 2.

Due to the results obtained with the synthesis of the two separate isomers, compounds 6i-6m where directly synthesized in the active (R)-(−) forms.

TABLE 2

Comparison between compounds 6c and 6d with their active isomers.

| | Code | | | | | |
|---|---|---|---|---|---|---|
| | 6c | (R)-(−)6c | (S)-(+)6c | 6d | (R)-(−)6d | (S)-(+)6d |
| IC$_{50}$ (nM) | 10.2 | 7 | >1000 | 80 | 53 | >1000 |

The results are expressed as Mean and 95% fiducial limits.

Capsaicin-Induced Secondary Allodynia in Rat

In a more extended study, compounds 6c and 6d were tested against capsaicin-induced secondary allodynia in rats. 90 Min after the capsaicin challenge, compounds 6c and 6d (both at 30 μmol/kg, p.o), significantly prevented the pro-allodinic effect of capsaicin (53.1% and 47.9% of inhibition, respectively).

ADME Studies

In order to select suitable drug candidates, ADME studies in vitro were performed on selected compounds 6c, 6d along with their active isomers, so as to assess the properties of these compounds according to the substituents.

LogD Values at pH=7.0 were calculated in silico, while the in vitro tests analysed:

metabolic stability in cryopreserved human hepatocytes;
cytotoxicity on Hep G2 cells;
cassette pharmacokinetics in rat.

The data of the compounds of the invention were compared to those obtained on two structurally different compounds recently disclosed as TRPV1 antagonists, namely JYL 1421 (Jakab et al., 2005) and SB-705498 (Rami et al., 2006) and to those obtained with two widely used drugs, one with short half life (naloxone) and one with long half-life (tolbutamide). The most relevant ADME data allow rapid comparison of the influence of specific substituents, especially on metabolic stability.

Hepatocytes Preparation

The cells were rapidly and carefully thawed and diluted in ice-cold Krebs-Henseleit Buffer (KHB). After centrifugation (50 g, 5 min.) the supernatant was discharged and the cells were resuspended in a volume of ice-cold KHB to a greater density than 2× (with respect to the final concentration of incubation) of viable cells/ml based on nominal concentration in cryopreserved vials. The viable cells were counted by Trypan Blue exclusion with a haemocytometer and the concentration of viable hepatocytes was accurately corrected to 2× concentration with KHB.

Hep G2 Cells Preparation

The cells were cultured for 3 days, trypsinized and re-suspended in 20 ml of culture medium. The cells were then counted and diluted to obtain a final concentration suitable for seeding 40.000 cells/well in 96-well cell culture plates (200 μl/well).

The cells were seeded in columns 1 to 11 (column 12 contained medium without cells), then placed for 16-24 hours at 37° C. with 5% of $CO_2$.

Compounds Preparation

Test and reference compounds were prepared at 2× incubation concentrations (10 and 1 μM) diluting 10 μl of stock solution in 0.99 ml of KHB to a concentration of 10 μM and 5 μl of stock solution in 0.995 μl of KHB to a concentration 5 μM. 300 μl of 10 μM and 1 μM solutions were then dispensed respectively in 2 and 1 incubation test tubes (Sterilin T.C. tube 17×100 mm).

Preliminary Cassette Pharmacokinetic Study in Catheterized Conscious Rats

Compounds were administered together to rats. The compounds were stored at −20° C. when not used. The formulation, route of administration, plasma samples identification and pharmacokinetic analysis were performed according to standard protocols (Raynaud, F I et al, 2004; Manitpisitkul, P. et al., 2004; Singh S. et al., 2006).

Results

With respect to compounds Ia, Ib, Ic disclosed in WO 2005/123666 A1, this new series of O-hydroxyalkyl urea derivatives showed a clear unexpected improvement in terms of metabolic stability and cytotoxicity comparable to reference compounds JYL 1421 and SB-705498 and a good half-life time, their clearance being relatively slow. Also cytotoxicity values expressed as micromolar $IC_{50}$ were acceptable. Table 3 reports the ADME profile of two compounds of the invention with respect to compounds disclosed in WO 2005/123666.

Furthermore, the (R)-(−)-isomers of compounds 6c and 6d showed a further improvement in terms of half-life, maintaining at the same time good values of metabolic stability and low cytotoxicity (Table 3).

TABLE 3

ADME profile of compounds 6c, 6d and their active isomers with the respect to selected reference compounds

| Code | Cytotoxicity in Hep G2 cells $IC_{50}$ μM | Metabolic stability in Human Hepatocytes $Cl_{int}$ | Pharmacokinetics in Rat Oral $t_{1/2}$ (min) |
|---|---|---|---|
| Ia [Ref. 1] | 21.9 | 1.81 | 19 |
| Ib [Ref. 1] | 22.2 | 2.19 | 14 |
| Ic [Ref. 1] | 18.3 | 2.21 | 19 |
| JYL 1421 | — | 0.9 | [Ref. 7] |
| SB-705498 | 20.3 | 0.33 | 180 [Ref. 8] |
| Naloxone | — | 1.99-2.30 | — |
| Tolbutamide | — | 0.04-0.38 | — |
| 6c | 52 | <1 | 78 |
| 6d | 70 | <1 | 65 |
| (R)-(−)6c | — | <1 | 462 |
| (R)-(−)6d | — | <1 | 266 |

REFERENCES

1. PharmEste S.r.I. WO 2005/123666 A1.
2. Bradford M M. Anal Biochem. 1976, 72, 248-254.
3. Munson P J. et al., Anal Biochem 1980, 107, 220-239.
4. Rigoni, M. et al., Br. J. Pharmacol. 2003, 138, 977-985.
5. Kudo, Y. et al., Jap. J. Pharmacol. 1986, 41, 345-351.
6. Chaplan N. et al., J Neurosci Methods. 1994, 53, 55-63
7. Jakab B. et al. Eur. J. Pharmacol. 2005, 517, 35-44.
8. Rami H K. et al. Bioorg. Med. Chem. Lett. 2006, 16, 3287-3291.
9. Raynaud F I. et al. Mol. Cancer. Ther. 2004, 3, 353-362.
10. Manitpisitkul, P. et al. Drug Discov. Today, 2004, 9, 652-658.
11. Singh S. Curr. Drug Metab. 2006, 7, 165-182.

The invention claimed is:

1. A compound of formula (I)

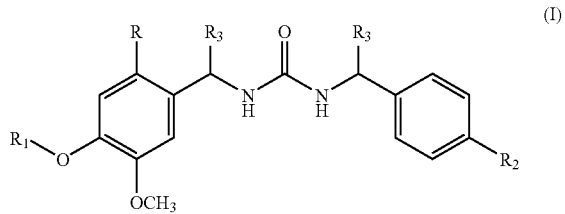

or an optical isomer or diastereoismer thereof,
in which
R is selected from halogen, alkyl, alkoxy, aryl and heteroaryl;
$R_1$ is selected from 2-hydroxyethyl, 2,3-dihydroxypropyl, 3-hydroxypropyl, 2,2-dihydroxyethyl, 3,3-dihydroxypropyl, 1,3-dioxolane-ethyl, 1,3-dioxane-methyl, 1,3- dioxolane-methyl, 1,3-dioxane-ethyl, 3-fluoro-2-hydroxypropyl, 3-carboxy-2-hydroxy-propyl, 3-chloro-2-hydroxypropyl, 2-hydroxypropyl, 2-hydroxy-propen-2-yl, morpholinoethyl, piperazinoethyl, hydroxymethyl, benzyl, 4-(hydroxymethyl)benzyl, 4-chlorobenzyl, 4-fluorobenzyl, and 4-hydroxybenzyl $R_2$ is tert-butyl or trifluoromethyl;

$R_3$ is independently selected from hydrogen, carboxy, alkyl, or hydroxyalkyl, wherein the halogen is a halogen atom selected from fluorine, chlorine, bromine and iodine;

the alkyl is a straight or branched $(C_1-C_4)$alkyl group;

the alkoxy is a straight or branched $(C_1-C_4)$alkoxy group;

the aryl is phenyl, optionally substituted with one or more halogen, alkyl, alkoxy groups as defined herein before, cyano or amino groups, which can be the same or different from one another; and the heteroaryl is a 5- or 6-membered heterocycle containing one or more nitrogen, oxygen or sulphur atoms, which can be the same or different from one another.

2. The compound according to claim 1 wherein:
R is chlorine or bromine;
$R_1$ is 2-hydroxyethyl;
$R_2$ is tert-butyl or trifluoromethyl;
$R_3$ is hydrogen.

3. The compound according to claim 1 wherein:
R is chlorine or bromine;
$R_1$ is 2,3-dihydroxypropyl;
$R_2$ is trifluoromethyl;
$R_3$ is hydrogen.

4. The compound according to claim 1 wherein:
R is methyl, phenyl, pyridine or 4-(substituted)-phenyl;
$R_1$ is (R)-(−)-2,3-dihydroxypropyl;
$R_2$ is trifluoromethyl;
$R_3$ is hydrogen.

5. The compound according to claim 1 wherein:
R is chlorine or bromine;
$R_1$ is (R)-(−)-2,3-dihydroxypropyl;
$R_2$ is trifluoromethyl;
$R_3$ is hydrogen.

6. A compound selected from the group consisting of:
1-[4-(2-hydroxyethoxy)-2-bromo-5-methoxybenzyl]-3-[4-(trifluoromethyl)-benzyl]urea;
1-[4-(2-hydroxyethoxy)-2-chloro-5-methoxybenzyl]-3-[4-(trifluoromethyl)-benzyl]urea;
1-[4-(2-hydroxyethoxy)-2-bromo-5-methoxybenzyl]-3-[4-(tert-butyl)-benzyl]urea;
1-[4-(2-hydroxyethoxy)-2-chloro-5-methoxybenzyl]-3-[4-(tert-butyl)-benzyl]urea;
1-[4-(2,3-dihydroxypropoxy)-2-chloro-5-methoxybenzyl]-3-[4-(trifluoromethyl)-benzyl]urea;
1-[4-(2,3-dihydroxypropoxy)-2-bromo-5-methoxybenzyl]-3-[4-(trifluoromethyl)-benzyl]urea;
1-[4-((R)-(−)-2,3-dihydroxypropoxy)-2-chloro-5-methoxybenzyl]-3-[4-(trifluoromethyl)-benzyl]urea;
1-[4-((R)-(−)-2,3-dihydroxypropoxy)-2-phenyl-5-methoxybenzyl]-3-[4-(trifluoromethyl)-benzyl]urea;
1-[4-((R)-(−)-2,3-dihydroxypropoxy)-2-(pyridin-3-yl)-5-methoxybenzyl]-3-[4-(trifluoromethyl)-benzyl]urea;
1-[4-((R)-(−)-2,3-dihydroxypropoxy)-2-(4-chlorophenyl)-5-methoxybenzyl]-3-[4-(trifluoromethyl)-benzyl]urea; and
1-[4-((R)-(−)-2,3-dihydroxypropoxy)-2-bromo-5-methoxybenzyl]-3-[4-(trifluoromethyl)-benzyl]urea.

7. A medicament comprising the compound according to claim 1.

8. A process for the preparation of pharmaceutical compositions for the therapy of inflammatory states, the process comprising admixing the compound according to claim 1 with suitable excipients and/or vehicles.

9. The process according to claim 8 wherein the inflammatory state is selected from the group consisting of chronic neuropathic pain, over-active bladder syndrome, tumour pain, hemorrhoids, inflammatory hyperalgesia, post-intervention pain, dental extraction, airway diseases, and gastrointestinal diseases.

10. Pharmaceutical compositions containing compounds according to claim 1, in admixture with suitable excipients and/or vehicles.

11. Vanilloid TRPV1 receptor antagonists comprising the compound according to claim 1.

12. A method to antagonize a vanilloid TRPV1 receptor, the method comprising contacting the compound according to claim 1 to the vanilloid receptor.

13. The method of claim 12, wherein the compound is selected from the group consisting of:
1-[4-(2-hydroxyethoxy)-2-bromo-5-methoxybenzyl]-3-[4-(trifluoromethyl)-benzyl]urea;
1-[4-(2-hydroxyethoxy)-2-chloro-5-methoxybenzyl]-3-[4-(trifluoromethyl)-benzyl]urea;
1-[4-(2-hydroxyethoxy)-2-bromo-5-methoxybenzyl]-3-[4-(tert-butyl)-benzyl]urea;
1-[4-(2-hydroxyethoxy)-2-chloro-5-methoxybenzyl]-3-[4-(tert-butyl)-benzyl]urea;
1-[4-(2,3-dihydroxypropoxy)-2-chloro-5-methoxybenzyl]-3-[4-(trifluoromethyl)-benzyl]urea;
1-[4-(2,3-dihydroxypropoxy)-2-bromo-5-methoxybenzyl]-3-[4-(trifluoromethyl)-benzyl]urea;
1-[4-((R)-(−)-2,3-dihydroxypropoxy)-2-chloro-5-methoxybenzyl]-3-[4-(trifluoromethyl)-benzyl]urea;
1-[4-((R)-(−)-2,3-dihydroxypropoxy)-2-phenyl-5-methoxybenzyl]-3-[4-(trifluoromethyl)-benzyl]urea;
1-[4-((R)-(+2,3-dihydroxypropoxy)-2-(pyridin-3-yl)-5-methoxybenzyl]-3-[4-(trifluoromethyl)-benzyl]urea;
1-[4-((R)-(+2,3-dihydroxypropoxy)-2-(4-chlorophenyl)-5-methoxybenzyl]-3-[4-(trifluoromethyl)-benzyl]urea; and
1-[4-((R)-(+2,3-dihydroxypropoxy)-2-bromo-5-methoxybenzyl]-3-[4-(trifluoromethyl)-benzyl]urea.

14. The medicament of claim 7, wherein the compound is selected from the group consisting of:
1-[4-(2-hydroxyethoxy)-2-bromo-5-methoxybenzyl]-3-[4-(trifluoromethyl)-benzyl]urea;
1-[4-(2-hydroxyethoxy)-2-chloro-5-methoxybenzyl]-3-[4-(trifluoromethyl)-benzyl]urea;
1-[4-(2-hydroxyethoxy)-2-bromo-5-methoxybenzyl]-3-[4-(tert-butyl)-benzyl]urea;
1-[4-(2-hydroxyethoxy)-2-chloro-5-methoxybenzyl]-3-[4-(tert-butyl)-benzyl]urea;
1-[4-(2,3-dihydroxypropoxy)-2-chloro-5-methoxybenzyl]-3-[4-(trifluoromethyl)-benzyl]urea;
1-[4-(2,3-dihydroxypropoxy)-2-bromo-5-methoxybenzyl]-3-[4-(trifluoromethyl)-benzyl]urea;
1-[4-((R)-(+2,3-dihydroxypropoxy)-2-chloro-5-methoxybenzyl]-3-[4-(trifluoromethyl)-benzyl]urea;
1-[4-((R)-(+2,3-dihydroxypropoxy)-2-phenyl-5-methoxybenzyl]-3-[4-(trifluoromethyl)-benzyl]urea;
1-[4-((R)-(+2,3-dihydroxypropoxy)-2-(pyridin-3-yl)-5-methoxybenzyl]-3-[4-(trifluoromethyl)-benzyl]urea;
1-[4-((R)-(+2,3-dihydroxypropoxy)-2-(4-chlorophenyl)-5-methoxybenzyl]-3-[4-(trifluoromethyl)-benzyl]urea; and 1-[4-((R)-(+2,3-dihydroxypropoxy)-2-bromo-5-methoxybenzyl]-3-[4-(trifluoromethyl)-benzyl]urea.

15. A method for treating an inflammatory state in an individual, the method comprising administering to the individual a therapeutic effective amount of the compound according to claim 1.

16. The method of claim 15, wherein, the inflammatory state is selected from the group consisting of chronic neuropathic pain, over-active bladder syndrome, tumour pain, hemorrhoids, inflammatory hyperalgesia, post-intervention pain, dental extraction, airway diseases, and gastro-intestinal diseases.

17. The method of claim 15, wherein the compound is selected from the group consisting of:
- 1-[4-(2-hydroxyethoxy)-2-bromo-5-methoxybenzyl]-3-[4-(trifluoromethyl)-benzyl]urea;
- 1-[4-(2-hydroxyethoxy)-2-chloro-5-methoxybenzyl]-3-[4-(trifluoromethyl)-benzyl]urea;
- 1-[4-(2-hydroxyethoxy)-2-bromo-5-methoxybenzyl]-3-[4-(tert-butyl)-benzyl]urea;
- 1-[4-(2-hydroxyethoxy)-2-chloro-5-methoxybenzyl]-3-[4-(tert-butyl)-benzyl]urea;
- 1-[4-(2,3-dihydroxypropoxy)-2-chloro-5-methoxybenzyl]-3-[4-(trifluoromethyl)-benzyl]urea;
- 1-[4-(2,3-dihydroxypropoxy)-2-bromo-5-methoxybenzyl]-3-[4-(trifluoromethyl)-benzyl]urea;
- 1-[4-((R)-(−)-2,3-dihydroxypropoxy)-2-chloro-5-methoxybenzyl]-3-[4-(trifluoromethyl)-benzyl]urea;
- 1-[4-((R)-(−)-2,3-dihydroxypropoxy)-2-phenyl-5-methoxybenzyl]-3-[4-(trifluoromethyl)-benzyl]urea;
- 1-[4-((R)-(−)-2,3-dihydroxypropoxy)-2-(pyridin-3-yl)-5-methoxybenzyl]-3-[4-(trifluoromethyl)-benzyl]urea;
- 1-[4-((R)-(−)-2,3-dihydroxypropoxy)-2-(4-chlorophenyl)-5-methoxybenzyl]-3-[4-(trifluoromethyl)-benzyl]urea; and
- 1-[4-((R)-(−)-2,3-dihydroxypropoxy)-2-bromo-5-methoxybenzyl]-3-[4-(trifluoromethyl)-benzyl]urea.

18. The pharmaceutical composition according to claim 10, wherein the compound is selected from the group consisting of:
- 1-[4-(2-hydroxyethoxy)-2-bromo-5-methoxybenzyl]-3-[4-(trifluoromethyl)-benzyl]urea;
- 1-[4-(2-hydroxyethoxy)-2-chloro-5-methoxybenzyl]-3-[4-(trifluoromethyl)-benzyl]urea;
- 1-[4-(2-hydroxyethoxy)-2-bromo-5-methoxybenzyl]-3-[4-(tert-butyl)-benzyl]urea;
- 1-[4-(2-hydroxyethoxy)-2-chloro-5-methoxybenzyl]-3-[4-(tert-butyl)-benzyl]urea;
- 1-[4-(2,3-dihydroxypropoxy)-2-chloro-5-methoxybenzyl]-3-[4-(trifluoromethyl)-benzyl]urea;
- 1-[4-(2,3-dihydroxypropoxy)-2-bromo-5-methoxybenzyl]-3-[4-(trifluoromethyl)-benzyl]urea;
- 1-[4-((R)-(+2,3-dihydroxypropoxy)-2-chloro-5-methoxybenzyl]-3-[4-(trifluoromethyl)-benzyl]urea;
- 1-[4-((R)-(+2,3-dihydroxypropoxy)-2-phenyl-5-methoxybenzyl]-3-[4-(trifluoromethyl)-benzyl]urea;
- 1-[4-((R)-(+2,3-dihydroxypropoxy)-2-(pyridin-3-yl)-5-methoxybenzyl]-3-[4-(trifluoromethyl)-benzyl]urea;
- 1-[4-((R)-(+2,3-dihydroxypropoxy)-2-(4-chlorophenyl)-5-methoxybenzyl]-3-[4-(trifluoromethyl)-benzyl]urea; and
- 1-[4-((R)-(+2,3-dihydroxypropoxy)-2-bromo-5-methoxybenzyl]-3-[4-(trifluoromethyl)-benzyl]urea.

\* \* \* \* \*